(12) United States Patent
Courtiade et al.

(10) Patent No.: US 10,377,960 B2
(45) Date of Patent: Aug. 13, 2019

(54) LOW VISCOSITY LUBRICATING POLYOLEFINS

(71) Applicant: TOTAL MARKETING SERVICES, Puteaux (FR)

(72) Inventors: Marion Courtiade, Taluyers (FR); Julien Sanson, Lyons (FR); Alexandre Welle, Court-St-Etienne (BE); Martine Slawinski, Nivelles (BE); Jeroen Wassenaar, Huizingen (BE)

(73) Assignee: TOTAL MARKETING SERVICES, Puteaux (FR)

( * ) Notice: Subject to any disclaimer, the term of this patent is extended or adjusted under 35 U.S.C. 154(b) by 0 days.

(21) Appl. No.: 15/740,746

(22) PCT Filed: Jun. 29, 2016

(86) PCT No.: PCT/EP2016/065109
§ 371 (c)(1),
(2) Date: Dec. 28, 2017

(87) PCT Pub. No.: WO2017/001458
PCT Pub. Date: Jan. 5, 2017

(65) Prior Publication Data
US 2018/0187118 A1    Jul. 5, 2018

(30) Foreign Application Priority Data

Jun. 29, 2015 (FR) ..................... 15 56043

(51) Int. Cl.
| | | |
|---|---|---|
| *C10M 105/04* | (2006.01) |
| *B01J 31/14* | (2006.01) |
| *B01J 31/22* | (2006.01) |
| *B01J 23/44* | (2006.01) |
| *C07C 2/32* | (2006.01) |
| *C07C 5/03* | (2006.01) |
| *C10M 169/04* | (2006.01) |

(52) U.S. Cl.
CPC ........... *C10M 105/04* (2013.01); *B01J 23/44* (2013.01); *B01J 31/143* (2013.01); *B01J 31/146* (2013.01); *B01J 31/2295* (2013.01); *C07C 2/32* (2013.01); *C07C 5/03* (2013.01); *C10M 169/04* (2013.01); *B01J 2231/20* (2013.01); *B01J 2531/48* (2013.01); *C07C 2521/04* (2013.01); *C07C 2523/44* (2013.01); *C07C 2531/14* (2013.01); *C07C 2531/22* (2013.01); *C10M 2203/022* (2013.01); *C10M 2203/1025* (2013.01); *C10N 2220/022* (2013.01); *C10N 2220/025* (2013.01); *C10N 2230/02* (2013.01); *C10N 2230/06* (2013.01); *C10N 2230/10* (2013.01); *C10N 2230/18* (2013.01); *C10N 2230/36* (2013.01); *C10N 2230/50* (2013.01); *C10N 2230/54* (2013.01); *C10N 2240/04* (2013.01); *C10N 2240/044* (2013.01); *C10N 2240/10* (2013.01); *C10N 2270/00* (2013.01)

(58) Field of Classification Search
CPC .............. C10M 105/04; C10M 169/04; C10M 2203/022; C10M 2203/1025; B01J 23/44; B01J 31/143; B01J 31/2295; B01J 31/146; B01J 2531/48; B01J 2231/20; C07C 2/32; C07C 5/03; C07C 2521/04; C07C 2531/14; C07C 2531/22; C07C 2523/44; C10N 2230/50; C10N 2230/36; C10N 2230/18; C10N 2270/00; C10N 2240/044; C10N 2240/04; C10N 2230/06; C10N 2230/02; C10N 2220/025; C10N 2220/022; C10N 2230/10; C10N 2240/10; C10N 2230/54
See application file for complete search history.

(56) References Cited

U.S. PATENT DOCUMENTS

| 5,171,905 A | 12/1992 | Theriot | |
|---|---|---|---|
| 2011/0166052 A1* | 7/2011 | Hee ..................... | C10M 101/02 508/110 |

FOREIGN PATENT DOCUMENTS

| EP | 0 240 813 A2 | 10/1987 | |
|---|---|---|---|
| EP | 0 283 922 A2 | 9/1988 | |
| EP | 0283922 A2 * | 9/1988 | ........... C10M 111/04 |
| EP | 1 950 278 A1 | 7/2008 | |

OTHER PUBLICATIONS

French Search Report, dated Apr. 18, 2016, in French Application No. FR 1556043.
International Search Report, dated Sep. 7, 2016, in International Application No. PCT/EP2016/065109.

* cited by examiner

*Primary Examiner* — Taiwo Oladapo
(74) *Attorney, Agent, or Firm* — Knobbe, Martens, Olson & Bear, LLP

(57) ABSTRACT

A low viscosity oil has more than 50% by weight of 9-methylnonadecane. A lubricating composition has this low viscosity oil as base oil and, optionally, another base oil or an additive. The low viscosity oil has a kinematic viscosity at 100° C., measured by the ASTM D445 standard, of 0.5 to 2.5 $mm^2s^{-1}$. The low viscosity oil can be prepared using a metallocene catalyst, and the low viscosity oil can be used as high performance lubricant for lubrication in the field of motors, hydraulic fluids and gears, in particular bridges and transmissions.

17 Claims, No Drawings

LOW VISCOSITY LUBRICATING POLYOLEFINS

PRIORITY AND CROSS REFERENCE TO RELATED APPLICATIONS

This application is the U.S. National Phase Application under 35 U.S.C. § 371 of International Application No. PCT/EP2016/065109, filed Jun. 29, 2016, designating the U.S. and published as WO 2017/001458 A1 on Jan. 5, 2017, which claims the benefit of French Application No. FR 1556043, filed Jun. 29, 2015. Any and all applications for which a foreign or a domestic priority is claimed is/are identified in the Application Data Sheet filed herewith and is/are hereby incorporated by reference in their entirety under 37 C.F.R. § 1.57.

FIELD

The present disclosure generally relates to low viscosity lubricating polyolefins.

SUMMARY

The invention relates to a low viscosity oil comprising more than 50% by weight of 9-methylnonadecane and to a lubricating composition comprising this base oil and optionally another base oil or additive. This oil of the invention has kinematic viscosity at 100° C., measured as per standard ASTM D445, ranging from 0.5 to 2.5 mm$^2$·s$^{-1}$. The invention also relates to said low viscosity oil prepared following a particular method using a metallocene catalyst, and to the use of this oil as high-performance lubricant for lubrication in the fields of engines, hydraulic fluids, gearboxes, in particular drive axles and transmissions.

DETAILED DESCRIPTION

In the API classification of base oils, polyalphaolefins (PAOs) are referenced as Group IV base oils. Through a good trade-off between viscosity, volatility and cold start properties, these PAOs are increasingly more used in high performance lubricating formulas. In particular, this better trade-off is highly advantageous in comparison in particular with Group II mineral bases.

In general, PAOs are synthesised from different olefin monomers, particularly from $C_6$ to $C_{14}$ monomers, via acid catalysis or in the presence of a metallocene catalyst.

In general, to prepare low viscosity PAO products, notably having kinematic viscosity at 100° C., measured as per standard ASTM D445, ranging from 0.2 to 4 mm$^2$·s$^{-1}$ (grades 0.2 to 4), acid catalysts are used.

Methods are known for preparing PAOs via metallocene catalysis that generally lead to products of high viscosity having kinematic viscosity at 100° C., measured as per standard ASTM D445, ranging from to 40 to 150 mm$^2$·s$^{-1}$ (grades 40 to 150).

It is also important to have base oils with improved properties compared with known base oils, particularly with respect to Group II or Group III base oils.

In addition, the needs for high performance lubricants are on the increase. In particular due to increasingly severe conditions of use e.g. due to very high temperatures or mechanical stresses.

Longer oil change times and a reduction in the size of lubricating systems also lead to an increased need for high performance lubricants.

Energy efficiency, and in particular an improvement in the potential Fuel Eco (FE) of lubricants with a reduction in engine fuel consumption, in particular by motor vehicle engines, are objectives of ever increasing importance and lead to an increasing use of high performance lubricants.

The energy efficiency of automotive gearboxes significantly impacts engine fuel consumption. Therefore, the search for improvement in gearbox performance, though the lubricant, is a priority research area in the field of Fuel Eco.

High performance lubricants, and more specifically gearbox lubricants, must therefore have improved properties, in particular as regards kinematic viscosity, viscosity index, volatility, low temperature dynamic viscosity, compatibility with elastomers, cold pour point and coefficient of friction in an elasto-hydrodynamic lubrication regime (characteristic of the teeth and bearing contacts).

High performance lubricants must also have good deaeration and foaming properties. Thermal stability and oxidation resistance are also properties to be maintained or even improved for high performance lubricants.

Reduced toxicity and good miscibility with other lubricants or other materials are similarly properties to be sought after for high performance lubricants.

Additionally, methods for preparing improved PAOs must be also be developed, in particular to improve the yield or selectivity of these methods. An improvement in catalytic activity must also be targeted.

Methods for preparing PAOs should also allow control over molecular weight, polydispersity index and the distribution of the formed PAOs.

An improvement in characterization techniques of the different products formed at the time of PAO synthesis is also desirable, in particular for qualitative or quantitative analysis of the formed products.

There is therefore a need for high performance lubricants allowing a solution to be found to all or part of the problems with lubricants in the state of the art.

The invention therefore provides an oil having kinematic viscosity at 100° C., measured as per standard ASTM D445, ranging from 0.5 to 2.5 mm$^2$·s$^{-1}$, and comprising more than 50% by weight of a 1-decene dimer of formula (I):

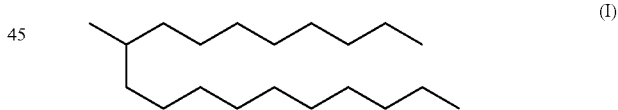

The oil of the invention has particularly advantageous viscosity ranging from 0.5 to 2.5 mm$^2$·s$^{-1}$. More advantageously, the kinematic viscosity of the oil of the invention ranges from 0.8 to 2.2 mm$^2$·s$^{-1}$. Preferably, the kinematic viscosity of the oil of the invention ranges from 1 to 2 mm$^2$·s$^{-1}$. More preferably, the kinematic viscosity of the oil of the invention is 1.6 mm$^2$·s$^{-1}$, 1.7 mm$^2$·s$^{-1}$ or 1.8 mm$^2$·s$^{-1}$.

Preferably, the oil of the invention has a mean molecular weight ranging from 150 to 1 000 g/mol, preferably from 180 to 500 g/mol. In general, according to the invention, the mean molecular weight is calculated according to standard ASTM D2502.

Also advantageously, the oil of the invention has a cold pour point of −10° C. or lower, preferably −15° C. or lower or −20° C. lower. In general, according to the invention the cold pour point is measured as per standard EN ISO 3016.

Advantageously, the oil of the invention comprises 50 to 99.9% by weight of 1-decene dimer of formula (I). Also advantageously, the oil of the invention comprises from 60 to 99.5% by weight or 70 to 99% by weight of 1-decene dimer of formula (I).

Preferably, the oil of the invention comprises at least 50% by weight of 1-decene dimer of formula (I), or at least 65 or 70% by weight of 1-decene dimer of formula (I). More advantageously, the oil of the invention comprises at least 80% by weight of 1-decene dimer of formula (I) or at least 90% by weight of 1-decene tetramer of formula (I).

In addition to the 1-decene dimer of formula (I), the oil of the invention may comprise other oligomers derived from the oligomerisation of 1-decene, in particular saturated oligomers. Thus, the oil of the invention may comprise at least one other saturated oligomer of 1-decene selected from among other saturated dimers of 1-decene (notably n-eicosan), saturated trimers of 1-decene, saturated tetramers of 1-decene, saturated pentamers of 1-decene. In particular, the oil of the invention may comprise at least one other saturated oligomer of 1-decene among the others saturated dimer of 1-decene; saturated trimer of 1-decene.

Also advantageously, the oil according to the invention comprises at least one other saturated dimer of 1-decene, preferably from 0.1 to 10% by weight of at least one other saturated dimer of 1-decene.

In particular, the oil according to the invention comprises
from 51 to 99.8% by weight of 1-decene dimer of formula (I);
from 0.1 to 10% by weight of at least one other saturated dimer of 1-decene;
from 0.1 to 2% by weight of at least one other saturated trimer of 1-decene.

The oil of the invention, as essential characteristic, comprises more than 50% by weight of 9-methylnonadecane, dimer of 1-decene of formula (I). Preferably, the oil of the invention comprising more than 50% by weight of 9-methylnonadecan is prepared following a method comprising:
oligomerisation of 1-decene in the presence of hydrogen ($H_2$), a metallocene catalyst and an activator compound, or in the presence of hydrogen ($H_2$), a metallocene catalyst, an activator compound and a co-activator compound;
catalytic hydrogenation of the oligomerisation products in the presence of hydrogen ($H_2$) and a catalyst selected from among a hydrogenation catalyst and a hydrogenation catalyst comprising palladium;
separation, via distillation at reduced pressure, of the fraction of dimers comprising more than 50% by weight of 1-decene dimer of formula (I):

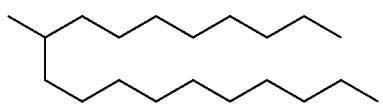
(I)

Preferably, oligomerisation of 1-decene is performed in the presence of a metallocene catalyst that is a racemic compound of formula (II)

(II)

where:
M is a transition metal selected from among titanium, zirconium, hafnium and vanadium, or it is zirconium;
$Q^1$ and $Q^2$, substituted or unsubstituted are independently a cyclic tetrahydroindenyl group, or $Q^1$ and $Q^2$ are independently a cyclic tetrahydroindenyl group and are linked to form a polycyclic structure;
L is a divalent $C_1$-$C_{20}$-alkyl group bridging $Q^1$ and $Q^2$ or L is a group selected from among methylene (—$CH_2$—), ethylene (—$CH_2$—$CH_2$—), methylmethylene (—$CH(CH_3)$—), 1-methyl-ethylene (—$CH(CH_3)$—$CH_2$—), n-propylene (—$CH_2$—$CH_2$—$CH_2$—), 2-methylpropylene (—$CH_2$—$CH(CH_3)$—$CH_2$—), 3-methylpropylene (—$CH_2$—$CH_2$—$CH(CH_3)$—), n-butylene (—$CH_2$—$CH_2$—$CH_2$—$CH_2$—), 2-methylbutylene (—$CH_2$—$CH(CH_3)$—$CH_2$—$CH_2$—), 4-methylbutylene (—$CH_2$—$CH_2$—$CH_2$—$CH(CH_3)$—), pentylene and isomers thereof, hexylene and isomers thereof, heptylene and isomers thereof, octylene and isomers thereof, nonylene and isomers thereof, decylene and isomers thereof, undecylene and isomers thereof, dodecylene and isomers thereof;
$R^1$ and $R^2$, substituted or unsubstituted, are independently an atom or a group selected from among hydrogen, halogens (such as Cl and I), alkyl (such as Me, Et, nPr, iPr), alkenyl, alkynyl, haloalkyl, haloalkenyl, haloalkynyl, silylalkyl, silylalkenyls, silylalkynyls, germylalkyl, germylalkenyl, germylalkynyl; or $R^1$ and $R^2$ together with M form a metallocycle having 3 to 20 carbon atoms.

More preferably, the metallocene catalyst is a racemic compound of formula (II) where:
M is zirconium;
$Q^1$ and $Q^2$, substituted or unsubstituted are independently a cyclic tetrahydroindenyl group;
L is a group selected from among methylene (—$CH_2$—), ethylene (—$CH_2$—$CH_2$—), methylmethylene (—$CH(CH_3)$—), 1-methyl-ethylene (—$CH(CH_3)$—$CH_2$—), n-propylene (—$CH_2$—$CH_2$—$CH_2$—), 2-methylpropylene (—$CH_2$—$CH(CH_3)$—$CH_2$—), 3-methylpropylene (—$CH_2$—$CH_2$—$CH(CH_3)$—), n-butylene (—$CH_2$—$CH_2$—$CH_2$—$CH_2$—), 2-methylbutylene (—$CH_2$—$CH(CH_3)$—$CH_2$—$CH_2$—), 4-methylbutylene (—$CH_2$—$CH_2$—$CH_2$—$CH(CH_3)$—), pentylene and isomers thereof, hexylene and isomers, heptylene and isomers thereof, octylene and isomers thereof, nonylene and isomers thereof, decylene and isomers thereof, undecylene and isomers thereof, dodecylene and isomers thereof;
$R^1$ and $R^2$, substituted or unsubstituted are independently a halogen atom such as Cl and I, or an alkyl group such as Me, Et, nPr, iPr.

Further preferably, the metallocene catalyst is selected from among rac-ethylene bis(tetrahydroindenyl) zirconium dimethyl and rac-ethylene bis(tetrahydroindenyl)zirconium dichloride, in particular rac-ethylene bis(tetrahydroindenyl) zirconium dimethyl.

For the method of the invention, the catalyst is used in activated form during oligomerisation of 1-decene. The invention therefore uses an activator compound during oligomerisation of 1-decene.

Advantageously, the activator compound is selected from among an alumoxane, an ionic activator and mixtures thereof.

Preferably, for the method of the invention, alumoxane is an oligomeric compound comprising residues of formula —Al(R)—O— where R is independently a cyclic or straight-chain $C_1$-$C_{20}$ alkyl group. Preferably, the alumoxane is selected from among methylalumoxane, modified methylalumoxane, ethylalumoxane, isobutylalumoxane and mixtures thereof.

Also preferably, the alumoxane is used in an alumoxane/catalyst molar ratio ranging from 1 to 10 000, preferably ranging from 10 to 3 000 and more preferably from 100 to 1 500. Preferably, for the method of the invention, the activator compound is an ionic activator. The ionic activator can be selected from among dimethylanilinium tetrakis-(perfluorophenyl)borate (DMAB), triphenylcarbonium tetrakis-(perfluorophenyl)borate, dimethylanilinium tetrakis-(perfluorophenyl)aluminate and mixtures thereof. More preferably, the ionic activator is dimethylanilinium tetrakis-(perfluorophenyl)borate (DMAB).

Also preferably, the ionic activator is used in an ionic activator/catalyst molar ratio ranging from 0.5 to 4, and preferably from 0.8 to 1.2.

For the oligomerisation of 1-decene, the method of the invention uses an activator compound. It may also be advantageous to use a co-activator compound, in particular if an ionic activator is used.

Preferably, the co-activator compound is a trialkylaluminium derivative. More preferably, the co-activator compound is selected from among tri-ethyl aluminium (TEAL), tri-iso-butyl aluminium (TIBAL), tri-methyl aluminium (TMA), tri-n-octyl aluminium and methyl-methyl-ethyl aluminium (MMEAL). Advantageously, tri-iso-butyl aluminium (TIBAL) is used in the form of a dispersion possibly ranging from 10 to 60% by weight.

Also preferably, the co-activator compound is used in a co-activator/catalyst molar ratio ranging from 10 to 1 000, preferably from 20 to 200.

Advantageously, the metallocene catalyst and the activator compound, optionally in the presence of a co-activator compound, are placed in contact at a pressure of 1 bar and at a temperature of 20° C.

Advantageously, oligomerisation of 1-decene is conducted for a time ranging from 2 to 300 min. Preferably, oligomerisation time ranges from 5 to 180 min, in particular from 30 to 140 min.

Also advantageously, oligomerisation of 1-decene is conducted in the presence of hydrogen ($H_2$) at a partial pressure ranging from 0.1 to 20 bar. Preferably the partial pressure of hydrogen ranges from 1 to 6 bar.

Also advantageously, oligomerisation is performed with a hydrogen/1-decene mass ratio higher than 100 ppm or lower than 600 ppm. Preferably, this ratio is between 100 and 600 ppm.

Also advantageously, oligomerisation of 1-decene is conducted at a temperature ranging from 50 to 200° C., preferably from 70 to 160° C. More preferably, the temperature during oligomerisation of 1-decene ranges from 80 to 150° C., and more preferably from 90 to 140° C. or from 100 to 130° C.

Oligomerisation of 1-denene can be performed in the 1-decene used as medium for the reaction. The reaction is then advantageously conducted in the absence of any solvent. Oligomerisation of 1-decene can also be conducted in a solvent. Preferably, the solvent can be selected from among a straight-chain or branched hydrocarbon, a cyclic or non-cyclic hydrocarbon, an alkylated aromatic compound and mixtures thereof. As preferred solvents for oligomerisation of 1-decene, preference is given to a solvent from among butanes, pentanes, hexanes, heptanes, octanes, cyclopentane, cyclohexane, methylcyclopentane, methylcyclohexane, methylcycloheptane, toluene, xylene and mixtures thereof.

After oligomerisation of 1-decene, the method of the invention applies catalytic hydrogenation of the oligomerisation products. Catalytic hydrogenation of the oligomerisation products is performed in the presence of hydrogen ($H_2$) and a hydrogenation catalyst.

Preferably, the hydrogenation catalyst is selected from among a palladium derivative, supported palladium derivative, alumina-supported palladium derivative (e.g. on gamma-alumina), nickel derivative, supported nickel derivative, kieselguhr-supported nickel derivative, platinum derivative, supported platinum derivative, cobalt-molybdenum derivative, supported cobalt-molybdenum derivative.

More preferably, the hydrogenation catalyst comprises palladium. One particularly preferred hydrogenation catalyst comprises alumina-supported palladium (e.g. on gamma-alumina).

Also preferably, the pressure of hydrogen ($H_2$) for catalytic hydrogenation of the oligomerisation products ranges from 5 to 50 bar, more preferably from 10 to 40 bar, in particular from 15 to 25 bar.

After oligomerisation of 1-decene and catalytic hydrogenation of the oligomerisation products, the method of the invention comprises separation via distillation at reduced pressure of the faction of dimers comprising more than 50% by weight of 1-decene dimer of formula (I).

Separation via distillation is performed at reduced pressure. Advantageously, separation via distillation is performed in accordance with standard ASTM D2892. In a preferred manner, the separation by distillation according to ASTM D2892 is carried out with an initial boiling point (IBP) of less than 375° C., preferably between 320 and 375° C. or between 340 and 350° C. The partial pressure is advantageously less than 0.67 mbar.

Preferably, the separation via distillation according to standard ASTM D2892 allows separation of the fraction of dimers comprising more than 50% by weight of 1-decene dimer of formula (I).

Therefore, separation via distillation at reduced pressure allows separation of the fraction of dimers resulting from oligomerisation of 1-decene, followed by hydrogenation of the oligomerisation products. This fraction of dimers comprises more than 50% by weight of 1-decene dimer of formula (I).

In addition to the steps of oligomerising 1-decene, catalytic hydrogenation of the oligomerisation products and separation via distillation at reduced pressure of the fraction of dimers comprising more than 50% by weight of 1-decene dimer of formula (I), the method of the invention may advantageously comprise other steps. For example, the method of the invention may also combine all or part of the following steps:

prior preparation of the 1-decene via catalytic oligomerisation of ethylene;

deactivation of the catalyst after oligomerisation of 1-decene or after catalytic hydrogenation of the oligomerisation products;

a final hydrogenation step of the fraction of dimers comprising more than 50% by weight of 1-decene dimer of formula (I) in the presence of hydrogen ($H_2$) and a catalyst selected from among a hydrogenation catalyst and a hydrogenation catalyst comprising palladium.

The prior preparation of 1-decene via catalytic oligomerisation of ethylene is known per se. It may prove to be particularly advantageous in combination with the other steps of the method of the invention. This prior preparation of 1-decene via catalytic oligomerisation of ethylene notably allows the use of more abundant sources of the starting substrate.

Also, and preferably, once oligomerisation of 1-decene is completed, the method of the invention may comprise deactivation of the catalyst. Deactivation of the oligomerisation catalyst can be carried out after oligomerisation of 1-décène or after catalytic hydrogenation of the oligomerisation products. Preferably, deactivation of the oligomerisation catalyst is performed after oligomerisation of 1-decene and before catalytic hydrogenation of the oligomerisation products.

Advantageously, deactivation of the catalyst is obtained by action of air or water or by means of at least one alcohol or a solution of deactivating agent. Preferably, deactivation of the catalyst is obtained by means of an alcohol e.g. isopropanol.

Also preferably, the method of the invention may comprise a final hydrogenation step of the fraction of dimers comprising more than 50% by weight of 1-decene dimer of formula (I). This final hydrogenation is performed in the presence of hydrogen ($H_2$) and a hydrogenation catalyst.

Preferably, the hydrogen catalyst is selected from among a palladium derivative, supported-palladium derivative, alumina-supported palladium derivative (e.g. on gamma-alumina), nickel derivative, supported nickel derivative, kieselguhr-supported nickel derivative, platinum derivative, supported platinum derivative, cobalt-molybdenum derivative, supported cobalt-molybdenum derivative. More preferably the hydrogenation catalyst comprises palladium. One particularly preferred catalyst comprises alumina-supported palladium (e.g. gamma-alumina). The hydrogenation catalyst is advantageously identical to the hydrogenation catalyst used for the hydrogenation following after oligomerisation of 1-decene. Advantageously, for final hydrogenation, the pressure of hydrogen ($H_2$) ranges from 5 to 50 bar or from 10 to 40 bar, preferably from 15 to 25 bar.

Also advantageously, for final hydrogenation, the hydrogenating time is between 2 and 600 min, preferably between 30 and 300 min.

Advantageously, for final hydrogenation, the temperature ranges from 50 to 200° C. or from 60 to 150° C. Preferably the temperature ranges from 70 to 140° C. or from 80 to 120° C.

Preferably, the oil of the invention is prepared according to a method wherein:
  oligomerisation of 1-decene is conducted for a time ranging from 2 to 300 min or from 5 to 180 min or from 30 to 140 min; or
  oligomerisation of 1-decene is conducted in the presence of hydrogen ($H_2$) at partial pressure ranging from 0.1 to 20 bar, or from 1 to 6 bar; or
  oligomerisation is conducted with a hydrogen/1-decene mass ratio higher than 100 ppm or lower than 600 ppm, or it is between 100 and 600 ppm; or
  oligomerisation of 1-decene is conducted at a temperature ranging from 50 to 200° C. or from 70 to 160° C. or from 80 to 150° C. or from 90 to 140° C. or from 100 to 130° C.; or
  the metallocene catalyst is a racemic compound of formula (II)

$$L(Q^1)(Q^2)MR^1R^2 \qquad (II)$$

where:
  M is a transition metal selected from among titanium, zirconium, hafnium and vanadium, or it is zirconium;
  $Q^1$ and $Q^2$, substituted or unsubstituted are independently a cyclic tetrahydroindenyl group or $Q^1$ and $Q^2$ are independently a cyclic tetrahydroindenyl group and are linked to form a polycyclic structure;
  L is a divalent $C_1$-$C_{20}$-alkyl group bridging $Q^1$ and $Q^2$, or L is a group selected from among methylene (—$CH_2$—), ethylene (—$CH_2$—$CH_2$—), methylmethylene (—CH($CH_3$)—), 1-methyl-ethylene (—CH($CH_3$)—$CH_2$—), n-propylene (—$CH_2$—$CH_2$—$CH_2$—), 2-methylpropylene (—$CH_2$—CH($CH_3$)—$CH_2$—), 3-methylpropylene (—$CH_2$—$CH_2$—CH($CH_3$)—), n-butylene (—$CH_2$—$CH_2$—$CH_2$—$CH_2$—), 2-methylbutylene (—$CH_2$—CH($CH_3$)—$CH_2$—$CH_2$—), 4-methylbutylene (—$CH_2$—$CH_2$—$CH_2$—CH($CH_3$)—), pentylene and isomers thereof, hexylene and isomers thereof, heptylene and isomers thereof, octylene and isomers thereof, nonylene and isomers thereof, decylene and isomers thereof, undecylene and isomers thereof, dodecylene and isomers thereof;
  $R^1$ and $R^2$, substituted or unsubstituted are independently an atom or a group selected from among hydrogen, halogens (such as Cl and I), alkyl (such as Me, Et, nPr, iPr), alkenyl, alkynyl, haloalkyl, haloalkenyl, haloalkynyl, silylalkyl, silylalkenyls, silylalkynyls, germylalkyl, germylalkenyl, germylalkynyl; or $R^1$ and $R^2$ together with M form a metallocycle having 3 to 20 carbon atoms; or
  the metallocene catalyst is selected from among rac-ethylene bis(tetrahydroindenyl) zirconium dimethyl and rac-ethylene bis(tetrahydroindenyl)zirconium dichloride; or
  oligomerisation of 1-decene is conducted in a solvent selected from among a straight-chain or branched hydrocarbon, cyclic or non-cyclic hydrocarbon, an alkylated aromatic compound and mixtures thereof, or in a solvent selected from among butanes, pentanes, hexanes, heptanes, octanes, cyclopentane, cyclohexane, methylcyclopentane, methylcyclohexane, methylcycloheptane, toluene, xylene and mixtures thereof; or
  the activator compound is selected from among an ionic activator and an oligomeric compound comprising residues of formula —Al(R)—O— where R is independently a cyclic or straight-chain $C_1$-$C_{20}$ alkyl group; or
  the activator compound is selected from among methylalumoxane, modified methylalumoxane, ethylalumoxane, isobutylalumoxane and mixtures thereof; or
  the activator compound is selected from among dimethylanilinium tetrakis(perfluorophenyl)borate (DMAB), triphenylcarbonium tetrakis(perfluorophenyl)borate, dimethylanilinium tetrakis(perfluorophenyl)aluminate and mixtures thereof; or
  the co-activator compound is a trialkylaluminium derivative or a compound selected from among tri-ethyl aluminium (TEAL), tri-iso-butyl aluminium (TIBAL), tri-methyl aluminium (TMA), tri-n-octyl aluminium and methyl-methyl-ethyl aluminium (MMEAL); or
  deactivation of the catalyst is performed by action of air or water, or by means of at least one alcohol or a solution of deactivating agent; or
  the pressure of hydrogen ($H_2$) for catalytic hydrogenation of the oligomerisation products ranges from 5 to 50 bar or from 10 to 40 bar or from 15 to 25 bar; or
  the hydrogenation catalyst is selected from among a palladium derivative, supported palladium derivative, alumina-supported palladium derivative (e.g. on gamma-alumina), nickel derivative, supported nickel derivative, kieselguhr-supported nickel derivative, platinum derivative, supported platinum derivative, cobalt-molybdenum derivative, supported cobalt-molybdenum derivative; or the pressure of hydrogen (H$_2$) at final hydrogenation of the majority fraction by weight of 1-decene dimer of formula (I) ranges from 5 to 50 bar or from 10 to 40 bar or from 15 to 25 bar; or the hydrogenating time for the final hydrogenation is between 2 and 600 min or between 30 and 300 min; or final hydrogenation is conducted at a temperature ranging from 50 to 200° C. or from 60 to 150° C. or from 70 to 140° C. or from 80 to 120° C.; or the hydrogenation catalyst for final hydrogenation of the fraction of dimers comprising more than 50% by weight of 1-decene dimer of formula (I), is selected from among a palladium derivative, supported palladium derivative, alumina-supported palladium derivative (e.g. on gamma-alumina), nickel derivative, supported nickel derivative, kieselguhr-supported nickel derivative, platinum derivative, supported platinum derivative, cobalt-molybdenum derivative, supported cobalt-molybdenum derivative.

More preferably, the oil of the invention is prepared according to a method combining all these characteristics.

Preferably, the oil of the invention is prepared following a method comprising:

oligomerisation of 1-decene in the presence of hydrogen (H$_2$), a metallocene catalyst and an activator compound, or in the presence of hydrogen (H$_2$), a metallocene catalyst, an activator compound and a co-activator compound;

catalytic hydrogenation of the oligomerisation products in the presence of hydrogen (H$_2$) and a catalyst selected from among a hydrogenation catalyst and a hydrogenation catalyst comprising palladium;

separation, via distillation at reduced pressure, of the fraction of dimers comprising more than 50% by weight of 1-decene dimer of formula (I).

More preferably, the oil of the invention is prepared with a method combining all these characteristics.

More preferably, the oil of the invention is prepared following a method wherein:

oligomerisation of 1-decene is performed for a time ranging from 2 to 300 min or from 5 to 180 min or from 30 to 140 min;

oligomerisation of 1-decene is performed in the presence of hydrogen (H$_2$) at partial pressure ranging from 0.1 to 20 bar or from 1 to 6 bar;

oligomerisation of 1-decene is conducted with a hydrogen/1-decene mass ratio higher than 100 ppm or lower than 600 ppm, or between 100 and 600 ppm; or oligomerisation of 1-decene is conducted at a temperature ranging from 50 to 200° C. or from 70 to 160° C. or from 80 to 150° C. or from 90 to 140° C. or from 100 to 130° C.;

the metallocene catalyst is a racemic compound of formula (II)

$$L(Q^1)(Q^2)MR^1R^2 \qquad (II)$$

where:

M is a transition metal selected from among titanium, zirconium, hafnium and vanadium, or it is zirconium;

Q$^1$ and Q$^2$, substituted or unsubstituted are independently a cyclic tetrahydroindenyl group, or Q$^1$ and Q$^2$ are independently a cyclic tetrahydroindenyl group and are linked to form a polycyclic structure;

L is a divalent C$_1$-C$_{20}$-alkyl group bridging Q$^1$ and Q$^2$, or L is a group selected from among methylene (—CH$_2$—), ethylene (—CH$_2$—CH$_2$—), methylmethylene (—CH(CH$_3$)—), 1-methyl-ethylene (—CH(CH$_3$)—CH$_2$—), n-propylene (—CH$_2$—CH$_2$—CH$_2$—), 2-methylpropylene (—CH$_2$—CH(CH$_3$)—CH$_2$—), 3-methylpropylene (—CH$_2$—CH$_2$—CH(CH$_3$)—), n-butylene (—CH$_2$—CH$_2$—CH$_2$—CH$_2$—), 2-methylbutylene (—CH$_2$—CH(CH$_3$)—CH$_2$—CH$_2$—), 4-methylbutylene (—CH$_2$—CH$_2$—CH$_2$—CH(CH$_3$)—), pentylene and isomers thereof, hexylene and isomers thereof, heptylene and isomers thereof, octylene and isomers thereof, nonylene and isomers thereof, decylene and isomers thereof, undecylene and isomers thereof, dodecylene and isomers thereof;

R$^1$ and R$^2$, substituted or unsubstituted are independently an atom or a group selected from among hydrogen, halogens (such as Cl and I), alkyl (such as Me, Et, nPr, iPr), alkenyl, alkynyl, haloalkyl, haloalkenyl, haloalkynyl, silylalkyl, silylalkenyls, silylalkynyls, germylalkyl, germylalkenyl, germylalkynyl; or R$^1$ and R$^2$ together with M form a metallocycle having 3 to 20 carbon atoms; or the metallocene catalyst is selected from among rac-ethylene bis(tetrahydroindenyl) zirconium dimethyl and rac-ethylene bis(tetrahydroindenyl)zirconium dichloride;

oligomerisation of 1-decene is performed in a solvent selected from among a straight-chain or branched hydrocarbon, a cyclic or non-cyclic hydrocarbon, an alkylated aromatic compound and mixtures thereof, or in a solvent selected from among butanes, pentanes, hexanes, heptanes, octanes, cyclopentane, cyclohexane, methylcyclopentane, methylcyclohexane, methylcycloheptane, toluene, xylene and mixtures thereof;

the activator compound is selected from among an ionic activator and an oligomeric compound comprising residues of formula —Al(R)—O— where R is independently a C$_1$-C$_{20}$ alkyl group, cyclic or straight-chain; or the activator compound is selected from among methylalumoxane, modified methylalumoxane, ethylalumoxane, isobutylalumoxane and mixtures thereof; or the activator compound is selected from among dimethylanilinium tetrakis(perfluorophenyl)borate, triphenylcarbonium tetrakis(perfluorophenyl)borate, dimethylanilinium tetrakis(perfluorophenyl)aluminate and mixtures thereof;

the co-activator compound is a trialkylaluminium derivative or a compound selected from among tri-ethyl aluminium (TEAL), tri-iso-butyl aluminium (TIBAL), tri-methyl aluminium (TMA), tri-n-octyl aluminium and methyl-methyl-ethyl aluminium (MMEAL);

deactivation of the catalyst is obtained by action of air or water, or by means of at least one alcohol or a solution of deactivating agent; or the pressure of hydrogen (H$_2$) for catalytic hydrogenation of the oligomerisation products ranges from 5 to 50 bar or from 10 to 40 bar or from 15 to 25 bar;

the hydrogenation catalyst is selected from among a palladium derivative, supported palladium derivative, alumina-supported palladium derivative (e.g. on gamma-alumina), nickel derivatise, supported nickel derivative, kieselguhr-supported nickel derivative, platinum derivative, supported platinum derivative, cobalt-molybdenum derivative, supported cobalt-molybdenum derivative;

the pressure of hydrogen ($H_2$) for final hydrogenation of the majority fraction by weight of 1-decene dimer of formula (I) ranges from 5 to 50 bar or from 10 to 40 bar or from 15 to 25 bar;

the hydrogenating time for final hydrogenation is between 2 and 600 min or between 30 and 300 min;

final hydrogenation is conducted at a temperature ranging from 50 to 200° C. or from 60 to 150° C. or from 70 to 140° C. or from 80 to 120° C.;

the hydrogenation catalyst for final hydrogenation of the fraction of dimers comprising more than 50% by weight of 1-decene dimer of formula (I), is selected from among a palladium derivative, supported palladium derivative, alumina-supported palladium derivative (e.g. on gamma-alumina), nickel derivative, supported nickel derivative, kieselguhr-supported nickel derivative, platinum derivative, supported platinum derivative, cobalt-molybdenum derivative, supported cobalt-molybdenum derivative;

In addition to the oligomerisation steps of 1-decene, catalytic hydrogenation of the oligomerisation products and separation via distillation at reduced pressure of the fraction of dimers comprising more than 50% by weight of 1-decene dimer of formula (I), the method of the invention may advantageously comprise other steps. For example, the method of the invention may also combine all or part of the following steps:

prior preparation of 1-decene via catalytic oligomerisation of ethylene; or deactivation of the catalyst after oligomerisation of 1-decene or after catalytic hydrogenation of the oligomerisation products; or a final hydrogenation step of the fraction of dimers comprising more than 50% by weight of 1-decene dimer of formula (I) in the presence of hydrogen ($H_2$) and a catalyst selected from among a hydrogenation catalyst and a hydrogenation catalyst comprising palladium.

The invention also relates to the use of an oil of the invention as base oil or as lubricating base oil. This use therefore concerns an oil of low viscosity comprising more than 50% by weight of 9-methylnonadecane, a dimer of 1-decene of formula (I).

The invention also relates to the use of an oil of the invention to improve the Fuel Eco (FE) of a lubricant or to reduce the fuel consumption of a vehicle equipped with a transmission, including a bridge or a gearbox, preferably a manual gearbox, lubricated with this composition.

The invention also relates to the use of an oil of the invention to reduce the fuel consumption of an engine or to reduce the fuel consumption of a motor vehicle engine.

These uses also concern an oil of the invention such as defined by its advantageous, particular or preferred characteristics, and by the preparation method thereof.

The invention also relates to a lubricating composition comprising an oil of the invention. This lubricating composition therefore comprises a low-viscosity oil comprising more than 50% by weight of 9-methylnonadecane, a dimer de 1-decene of formula (I). Advantageously, the composition of the invention comprises at least 10% by weight or at least 20% by weight of an oil of the invention. Also advantageously, the composition of the invention comprises at least 30, 40, 50 or 60% by weight of an oil of the invention. Also advantageously, the composition of the invention comprise from 10 to 90% by weight, preferably from 10 to 80% by weight. The composition of the invention may also comprise from 10 to 20 or 30, 40 or 50% by weight of at least one base oil of the invention.

The invention also relates to a lubricating composition for transmissions, in particular for gearboxes, in particular for a manual gearbox, comprising from 10 to 90%, preferably from 10 to 80% by weight of oil according to the invention.

Also advantageously, the composition of the invention comprises an oil of the invention and at least one other base oil. It may also comprise an oil of the invention and at least one additive, notably a PPD agent (Pour-Point Depressant) or else an oil of the invention, at least one other base oil and at least one additive, notably a PPD agent.

The lubricating composition of the invention may comprise an oil of the invention such as defined by its advantageous, particular or preferred characteristics and by the preparation method thereof.

As other base oil combined with the oil of the invention, the composition of the invention may comprise an oil selected from among a Group II, notably a fluid Group II oil, a Group III oil, Group IV oil or a Group V oil, in particular esters and polyalkylene-glycols.

The lubricating composition according to the invention is particularly advantageous for use as a high performance lubricant for lubrication in the fields of engines, in particular for motor vehicles, hydraulic fluids, gears, in particular bridges and transmissions.

The lubricating composition according to the invention may also be used for the lubrication of industrial machines, such as compressors, aircraft engines or for low temperature lubrication.

The invention thus relates to the use of a lubricating composition of the invention to improve the Fuel Eco (FE) of a lubricant or to reduce the fuel consumption of a vehicle equipped with a transmission, in particular a bridge or a gearbox, preferably a manual gearbox, lubricated with this composition.

The invention also concerns the use of a lubricating composition of the invention to reduce the fuel consumption of an engine or to reduce the fuel consumption of a motor vehicle engine.

The invention also relates to the use of a lubricating composition according to the invention for reducing the traction coefficient of a transmission oil, particularly a gearbox oil, preferably a manual gearbox.

The different aspects of the invention are the subject of the following examples given for illustrative purposes.

EXAMPLES

An autoclave reactor was used equipped with an agitator, a temperature control system and inlets for adding nitrogen, hydrogen and 1-decene.

1-decene (produced by TCI or Acros) was used with purity higher than 94%. It was purified on 3 Å and 13× molecular sieves (Sigma-Aldrich). Before use, the molecular sieves were previously dried at 200° C. for 16 hours.

The products were characterized by $^1$H NMR and two-dimensional gas phase chromatography (GCxGC).

For NMR, the PAO samples were diluted in deuterated chloroform, and NMR spectra were obtained at 27° C. on Bruker 400 MHz spectrometers: $^1$H, $^{13}$C, HMQC (heteronuclear multiple quantum coherence) and HMBC (heteronuclear multiple bond coherence).

Two-dimensional chromatography was used in continuous mode using two apolar and polar columns. The entirety of the effluent leaving the first column was separated in the second dimension. Separation of the compounds was governed by volatility on the first column and by specific interactions (π-π type, dipolar interactions, etc) on the second dimension. As a function of their viscosity, the samples were generally diluted twice in heptane. The chromatographic conditions were optimised for elution of the PAOs prepared according to the invention. The samples were analysed by GCxGC with cryogenic modulation (liquid nitrogen), programming of the first oven from 45° C. (5 min) up to 320° C. (20 min) with a ramp of 3° C./min, programming of the secondary oven from 60° C. (5 min) up to 330° C. (20 min) with a ramp of 3° C./min; the columns used under the following conditions:

$1^{st}$ dimension: HP1, 25 m, ID 0.32 mm, film thickness: 0.17 μm;

$2^{nd}$ dimension: BPX-50, 1.5 m, ID 0.1 mm, film thickness: 0.1 μm;

injector: split 100:1, injected volume: 0.1 μl;

detector: FID, 320° C.;

temperature of hot jet: 320° C.;

cold jet programming from 80 to 5%;

modulation period: 4.8 s.

Example 1

An 8 L autoclave reactor was used. Before use, the reactor was dried at 130° C. under a stream of nitrogen for one hour, and cooled to 110° C. It was then filled with 3 500 mL of 1-decene under a stream of nitrogen. The temperature of the reactor was held at 110° C. and hydrogen ($H_2$) added in an m/m ratio of $H_2$/1-decene of 414 ppm.

The catalyst was rac-ethylene bis(tetrahydroindenyl) zirconium dimethyl activated with dimethylanilinium tetrakis (perfluorophenyl)borate (DMAB) in a B/Zr molar ratio of 1.75. Triisobutyl aluminium (TiBAl) was used as co-activator compound in an Al/Zr molar ratio of 200. It allowed trapping of impurities present in the reactor.

Oligomerisation was initiated at the time the activated catalyst was added in a concentration of 17 μM relative to the oligomerisation solution.

After 120 min, 5 mL of isopropanol were added to deactivate the catalyst.

Hydrogenation of the reaction products was performed using an alumina-supported palladium catalyst (5 g of palladium on gamma-alumina at 5% w/w relative to alumina—produced by Alfa Aesar) and hydrogen ($H_2$) at 20 bar, at a temperature of 100° C., for full hydrogenation (followed by NMR to control removal of unsaturations).

The oligomerisation products and the fraction of dimers comprising more than 50% by weight of 9-methylnonadecane were then separated via distillation at reduced pressure (0.67 mbar) as per standard ASTM D2892, using a column with 15 theoretical plates having a maximum temperature of 375° C. The distillation in accordance with standard ASTM D2892 then allows the separation of products having a boiling point of less than 375° C.

The 9-methylnonadecane content of the oil of the invention obtained is 92.50%.

This oil of the invention comprising more than 50% by weight of 9-methylnonadecane has kinematic viscosity at 100° C., measured as per standard ASTM D445, of 1.796 $mm^2 \cdot s^{-1}$.

The characteristics of the oil of the invention allow excellent lubricating, rheological properties to be obtained, as well as oxidation resistance and Fuel Eco properties.

Example 2, 3, 4—Comparative

Identical measurements and characterizations were performed on a reference commercial oils. This was an oil of Group II (product S-Oil Ultra S-2), comparative oil (1) and two PAO prepared from olefins via acid catalysis (products Ineos Durasyn 162) and ExxonMobil Chemical Spectrasyn 2), comparative oils (2) and their characteristics are described in Table 1.

TABLE 1

|  | Comparative oil | | |
| --- | --- | --- | --- |
|  | (1) | (2) | (3) |
| kinematic viscosity at 100° C. ($ASTM\ D445/mm^2 \cdot s^{-1}$) | 2.240 | 1.723 | 1.68 |
| flash point (NF EN ISO 2592/° C.) | 162 | / | 172 |

Example 5: Preparation of a Lubricating Composition According to the Invention (1) and of 3 Comparative Lubricating Compositions (1), (2) and (3) and Evaluation of the Characteristics of these Compositions Lubricating compositions were prepared by mixing the oil of Example 1 or a comparative oil (1), (2) and (3) with another base oil of Group III, viscosity-index improving polymers, and a mixture of additives (dispersants, friction modifier, detergents including sulfonate, antioxidant, pour point improver, anti-wear agent).

The lubricating compositions thus prepared are described in Table 2 (weight %).

TABLE 2

|  | Composition (1) of the invention | Composition comparative | | |
| --- | --- | --- | --- | --- |
|  |  | (1) | (2) | (3) |
| Group III base oil | 46.7 | 48.7 | 46.9 | 46.7 |
| oil (1) of the invention | 33.75 | 0 | 0 | 0 |
| comparative oil (1) | 0 | 33.75 | 0 | 0 |
| comparative oil (2) | 0 | 0 | 33.75 | 0 |
| comparative oil (3) | 0 | 0 | 0 | 33.75 |
| mixture of additives | 8.55 | 8.55 | 8.55 | 8.55 |
| polymers | 11 | 9 | 10.8 | 11 |

The characteristics of the prepared lubricating compositions were evaluated, and the results obtained are given in Table 3.

TABLE 3

|  | Composition (1) of the invention | Comparative composition | | |
| --- | --- | --- | --- | --- |
|  |  | (1) | (2) | (3) |
| kinematic viscosity at 100° C. (NF EN ISO 3104/ $mm^2 \cdot s^{-1}$) | 6.221 | 6.176 | 6.219 | 6.224 |
| viscosity index (ISO 2909) | 194 | 172 | 182 | 181 |

TABLE 3-continued

|  | Composition (1) of the invention | Comparative composition | | |
|---|---|---|---|---|
|  |  | (1) | (2) | (3) |
| flash point (NF EN ISO 2592/° C.) | 192 | 184 | 182 | 180 |
| Brookfield viscosity at −40° C. (NFT 60-152)/mPa · s | 12 100 | 50 400 | 11 600 | 8 100 |

The lubricating composition according to the invention has characteristics at least equivalent and generally superior to the characteristics of the comparative compositions (1), (2) and (3).

Example 6: Evaluation of the Properties of the Lubricating Composition According to the Invention (1)

The aeration characteristics of the lubricant composition (1) according to the invention are measured. The conditions and results are shown in Table 4.

TABLE 4

|  | Specification | Composition (1) according to the invention |
|---|---|---|
| foaming at 24° C. (ASTM D892/mL/mL) | 100 max/10 max | 20/0 |
| foaming at 94° C. (ASTM D892/mL/mL) | 100 max/10 max | 40/0 |
| foaming at 94° C. then at 24° C. (ASTM D892/mL/mL) | 100 max/10 max | 0/0 |
| foaming at 40° C. (ASTM D3427/min) | maximum 30 | 7 |

The measurements are effected during 192 hours to 150° C. (CEC L-48-A-00 method B for the measurements of variations) The results are given in Table 5 and thus indicate the variations between the oxidized oil and the new oil.

TABLE 5

|  | Spécification | Composition (1) of the invention |
|---|---|---|
| variation of kinematic viscosity at 40° C. (%) | maximum 50 | 17 |
| PAI (ASTM D7214/A · cm$^{-1}$ · mm) | / | 52 |

The compatibility of the lubricating composition (1) according to the invention with elastomers is evaluated (RE1 fluoroelastomer 150° C. according to CEC L39-T-96) and the results are shown in Table 6.

TABLE 6

|  | Spécification | Composition (1) of the invention |
|---|---|---|
| variation de volume (%) | 0 à 15 | 2.2 |
| variation de dureté (points) | −10 à 0 | −1 |

TABLE 6-continued

|  | Spécification | Composition (1) of the invention |
|---|---|---|
| résistance à la rupture (%) | / | −50.9 |
| allongement à la rupture (%) | / | −54.3 |

The lubricating composition of the invention has very good properties.

Example 7: Preparation of a Lubricating Composition According to the Invention (1) and of 3 Comparative Lubricating Compositions (1), (2) and (3) and Evaluation of the Properties of these Compositions for Lubricating the Transmission of a Motor Vehicle The tribological properties of the lubricating compositions are evaluated according to a tensile analysis by means of a Mini-Traction Machine MTM device (MTM conditions: T=40° C., traction speed $V_e$=1 m/s, SRR=20% load=75 N). The results are shown in Table 7. The lower the coefficient of traction, the better the performance of the lubricating composition.

TABLE 7

|  | Composition (1) of the invention | Comparative Composition | | |
|---|---|---|---|---|
|  |  | (1) | (2) | (3) |
| traction coefficient | 0.0373 | 0.0499 | 0.0433 | 0.0435 |

The lubricating composition according to the invention allows a much greater traction gain compared to lubricating compositions comprising known base oils.

In addition, the reduction in the amount of $CO_2$ emitted was estimated from the tensile coefficient, the kinematic viscosity at 100° C. and the viscosity index. A reference lubricant composition was used to compare the 4 lubricating compositions evaluated. The results are shown in Table 8.

TABLE 8

|  | Composition (1) of the invention | Comparative composition | | |
|---|---|---|---|---|
|  |  | (1) | (2) | (3) |
| yield gain (%) | 0.44 | 0.25 | 0.36 | 0.32 |

The lubricating composition according to the invention allows a much higher gain compared to lubricating compositions comprising known base oils.

Example 8: Evaluation of the Properties of the Lubricant Composition According to the Invention (1) and Comparative Lubricating Compositions (1) and (2) for the Lubrication of the Transmission of a Motor Vehicle The composition (1) according to the invention and the comparative compositions (1) and (2) were tested on a test bench for transmission fluid efficiency.

The test bench principle is to characterize the overall efficiency of a transverse gearbox (5-speed manual gearbox used in segment B vehicles). For this, the operation of a gearbox under conditions close to the actual conditions of use corresponding to the NEDC cycle is simulated (speeds ranging from 500 to 4000 rpm and torques ranging from 20 to 100 Nm). The torque is then measured at the output of the gearbox and the ratio between the input and the output torque defines the efficiency of the system. The higher this efficiency, the lower the energy losses in the gearbox and the lower the amount of $CO_2$ emitted. A test was also performed on a reference lubricating oil. For the three lubricating compositions evaluated, the yield gain was calculated with respect to this reference oil. As with efficiency, the higher the efficiency gain, the more it implies a reduction in the amount of $CO_2$ emitted. Table 9 summarizes the results in yield and yield gain for the composition (1) according to the invention and the comparative compositions (1) and (2).

TABLE 9

|  | Composition (1) according to the invention | Comparative composition | |
|---|---|---|---|
|  |  | (1) | (2) |
| Yield (%) | 96.01 | 95.75 | 95.89 |
| Yield gain (%) | 0.55 | 0.29 | 0.43 |

The lubricating composition according to the invention reveals a much higher efficiency of the transmission box compared to lubricating compositions comprising known base oils. The efficiency gains calculated in this way make it possible to confirm the results estimated in Table 8. The lubricating composition according to the invention therefore allows a significant reduction in the quantity of $CO_2$ emitted.

What is claimed is:

1. A lubricating base oil having kinematic viscosity at 100° C., measured as per standard ASTM D445, ranging from 0.5 to 2.5 $mm^2 \cdot s^{-1}$, comprising more than 50% by weight of 1-decene dimer of formula (I):

(I)

2. The oil according to claim 1, comprising from 50 to 99.9% by weight of 1-decene dimer of formula (I).

3. The oil according to claim 1, comprising at least 65% by weight of 1-decene dimer of formula (I).

4. The oil according to claim 1, further comprising at least one other saturated dimer of 1-decene.

5. The oil according to claim 1, comprising:
51 to 99.8% by weight of 1-decene dimer of formula (I);
0.1 to 10% by weight of at least one other saturated dimer of 1-decene;
0.1 to 2% by weight of at least one saturated trimer of 1-decene.

6. The oil according to claim 1, wherein the kinematic viscosity at 100° C., measured as per standard ASTM D445, ranges from 0.8 to 2.2 $mm^2 \cdot s^{-1}$.

7. The oil according to claim 1, comprising 1-decene dimer of formula (I) and prepared by a method comprising:
oligomerizing 1-decene in the presence of hydrogen ($H_2$), a metallocene catalyst and an activator compound, or in the presence of hydrogen ($H_2$), a metallocene catalyst, an activator compound and a co-activator compound;
catalytically hydrogenating the oligomerisation products in the presence of hydrogen ($H_2$) and a catalyst selected from the group consisting of a hydrogenation catalyst and a hydrogenation catalyst comprising palladium;
separating, via distillation at reduced pressure, the fraction of dimers comprising more than 50% by weight of 1-decene dimer of formula (I).

8. The oil according to claim 1, comprising 1-decene dimer of formula (I) and prepared by a method comprising:
oligomerizing 1-decene in the presence of hydrogen ($H_2$), a metallocene catalyst and an activator compound, or in the presence of hydrogen ($H_2$), a metallocene catalyst, an activator compound and a co-activator compound;
catalytically hydrogenating the oligomerisation products in the presence of hydrogen ($H_2$) and a catalyst selected from the group consisting of a hydrogenation catalyst and a hydrogenation catalyst comprising palladium;
separating, via distillation at reduced pressure, the fraction of dimers comprising more than 50% by weight of 1-decene dimer of formula (I);
wherein the method further comprises:
prior preparation of 1-decene via catalytic oligomerisation of ethylene; or
deactivation of the catalyst after oligomerisation of 1-decene or after catalytic hydrogenation of the oligomerisation products; or
a final hydrogenation step of the fraction of dimers comprising more than 50% by weight of 1-decene dimer of formula (I) in the presence of hydrogen ($H_2$) and a catalyst selected from the group consisting of a hydrogenation catalyst and a hydrogenation catalyst comprising palladium.

9. The oil according to claim 1, comprising 1-decene dimer of formula (I) and prepared by a method comprising:
oligomerizing 1-decene in the presence of hydrogen ($H_2$), a metallocene catalyst and an activator compound, or in the presence of hydrogen ($H_2$), a metallocene catalyst, an activator compound and a co-activator compound;
catalytically hydrogenating the oligomerisation products in the presence of hydrogen ($H_2$) and a catalyst selected from the group consisting of a hydrogenation catalyst and a hydrogenation catalyst comprising palladium;
separating, via distillation at reduced pressure, the fraction of dimers comprising more than 50% by weight of 1-decene dimer of formula (I),
wherein:
oligomerisation of 1-decene is performed in the presence of hydrogen ($H_2$) at partial pressure ranging from 0.1 to 20 bar; or
oligomerisation is performed with a hydrogen/1-decene mass ratio higher than 100 ppm or lower than 600 ppm, or
the metallocene catalyst is a racemic compound of formula (II)

$$L(Q^1)(Q^2)MR^1R^2 \qquad (II)$$

where:
M is a transition metal selected from the group consisting of titanium, zirconium, hafnium and vanadium;
$Q^1$ and $Q^2$, substituted or unsubstituted are independently a cyclic tetrahydroindenyl group, or $Q^1$ and $Q^2$ are independently a cyclic tetrahydroindenyl group and are linked to form a polycyclic structure;
L is a divalent $C_1$-$C_{20}$-alkyl group bridging $Q^1$ and $Q^2$, or L is a group selected from the group consisting of methylene (—$CH_2$—), ethylene (—$CH_2$—$CH_2$—), methylmethylene (—CH($CH_3$)—), 1-methyl-ethylene (—CH($CH_3$)—$CH_2$—), n-propylene (—$CH_2$—$CH_2$—$CH_2$—), 2-methylpropylene (—$CH_2$—CH($CH_3$)—

CH₂—), 3-methylpropylene (—CH₂—CH₂—CH(CH₃)—), n-butylene (—CH₂—CH₂—CH₂—CH₂—), 2-methylbutylene (—CH₂—CH(CH₃)—CH₂—CH₂—), 4-methylbutylene (—CH₂—CH₂—CH₂—CH(CH₃)—), pentylene and isomers thereof, hexylene and isomers thereof, heptylene and isomers thereof, octylene and isomers thereof, nonylene and isomers thereof, decylene and isomers thereof, undecylene and isomers thereof, dodecylene and isomers thereof;

$R^1$ and $R^2$, substituted or unsubstituted are independently an atom or a group selected from the group consisting of hydrogen, halogens (such as Cl and I), alkyl (such as Me, Et, nPr, iPr), alkenyl, alkynyl, haloalkyl, haloalkenyl, haloalkynyl, silylalkyl, silylalkenyls, silylalkynyls, germylalkyl, germylalkenyl, germylalkynyl; or $R^1$ and $R^2$ together with M form a metallocene having 3 to 20 carbon atoms; or the activator compound is selected from the group consisting of an ionic activator and an oligomeric compound comprising residues of formula —Al(R)—O— where R is independently a $C_1$-$C_{20}$ alkyl group, cyclic or straight-chain; or the activator compound is selected from among methylalumoxane, modified methylalumoxane, ethylalumoxane, isobutylalumoxane and mixtures thereof; or the activator compound is selected from among dimethylanilinium tetrakis(perfluorophenyl)borate (DMAB), triphenylcarbonium tetrakis(perfluorophenyl)borate, dimethylanilinium tetrakis(perfluorophenyl)aluminate and mixtures thereof; or the co-activator compound is a trialkylaluminium derivative, or a compound selected from the group consisting of tri-ethyl aluminium (TEAL), tri-iso-butyl aluminium (TIBAL), tri-methyl aluminium (TMA), tri-n-octyl aluminium and methyl-methyl-ethyl aluminium (MMEAL).

10. A lubricating composition comprising:
at least one base oil according to claim 1, at least one other base oil and at least one additive.

11. The lubricating composition according to claim 10, comprising at least 10% by weight of at least one base oil having kinematic viscosity at 100° C., measured as per standard ASTM D445, ranging from 0.5 to 2.5 mm²·s⁻¹, comprising more than 50% by weight of 1-decene dimer of formula (I):

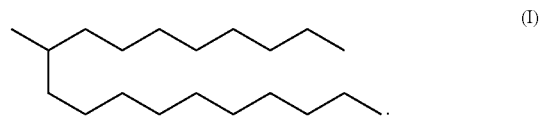 [SMILES: CCCCCCCCCCC(C)CCCCCCCC]

(I)

12. A method for reducing a fuel consumption of a vehicle equipped with a transmission comprising lubricating said transmission with the lubricating composition according to claim 11.

13. A method for reducing the fuel consumption of a vehicle equipped with a transmission comprising lubricating said transmission with the oil according to claim 1.

14. The oil according to claim 1, wherein the kinematic viscosity at 100° C., measured as per standard ASTM D445, is 1.7 mm²·s⁻¹.

15. The lubricating according to claim 10, wherein the additive is a PPD agent.

16. The oil according to claim 9, wherein M is zirconium.

17. The oil according to claim 9, wherein the oligomerisation of 1-decene is performed in the presence of hydrogen ($H_2$) at partial pressure ranging from 1 to 6 bar.

* * * * *